(12) United States Patent
Dryer et al.

(10) Patent No.: US 6,745,632 B1
(45) Date of Patent: Jun. 8, 2004

(54) METHOD FOR MEASURING ULTRASONIC TRANSIT TIMES

(76) Inventors: Joseph Ernest Dryer, 10307 Sugar Hill Dr., Houston, TX (US) 77042; John David Lambert, 24703 Lakebriar Dr., Katy, TX (US) 77494

(*) Notice: Subject to any disclaimer, the term of this patent is extended or adjusted under 35 U.S.C. 154(b) by 0 days.

(21) Appl. No.: 10/453,382

(22) Filed: Jun. 3, 2003

(51) Int. Cl.[7] .................. G01N 29/18; G01N 29/02
(52) U.S. Cl. .................. 73/597; 73/602; 73/861.06; 73/861.27; 73/861.28; 73/861.29
(58) Field of Search .................. 73/602, 597, 598, 73/861.06, 861.27, 861.28, 861.29, 861.31; 702/47, 54, 55, 109, 112

(56) References Cited

U.S. PATENT DOCUMENTS

| | | | | |
|---|---|---|---|---|
| 4,301,684 A | * | 11/1981 | Thompson et al. | ............ 73/602 |
| 4,307,616 A | * | 12/1981 | Vasile | ............ 73/643 |
| 4,837,578 A | * | 6/1989 | Gammell | ............ 342/194 |
| 5,042,303 A | * | 8/1991 | Geluk et al. | ............ 73/602 |
| 5,197,019 A | * | 3/1993 | Delon-Martin et al. | ...... 600/443 |
| 5,203,823 A | * | 4/1993 | Wadaka et al. | ............ 73/602 |
| 5,650,571 A | * | 7/1997 | Freud et al. | ............ 73/861.06 |
| 5,770,806 A | * | 6/1998 | Hiismaki | ............ 73/861.29 |
| 6,681,635 B1 | * | 1/2004 | Van Schaik | ............ 73/597 |

FOREIGN PATENT DOCUMENTS

DE  2643423 A  *  3/1978  ............ H04N/7/02

* cited by examiner

Primary Examiner—Hezron Williams
Assistant Examiner—Rose M. Miller

(57) ABSTRACT

Embodiments of the invention provide an algorithm for enhancing the transit time measurement of an ultrasonic wave through a fluid, and criteria for evaluating the suitability for various waveforms with regard to noise rejection. The transit time calculation provides a greater noise immunity and accuracy than techniques used in the prior art, and allows a measure of weighting of dispersed signals with different arrival times. The transit time calculation utilizes either the transmitted signal or the measurement of a reference system, the calculation of the squared convolution of this signal with the received signal, and the calculation of the transit time from the time-weighted squared convolution signal over a suitable interval defined by the minimums of the squared convolution signal. In the case of dispersion where the arrival times are symmetrically displaced around a mean transit time, or if asymmetric dispersion is suitably within the main lobe, the calculation properly weights the composite signal. The symmetry of the calculated autocorrelation function predicts the accuracy of the algorithm, and deconvolution can be used to estimate the composition of the composite delay function in such cases.

11 Claims, 11 Drawing Sheets

METHOD FOR MEASURING ULTRASONIC TRANSIT TIMES

CROSS-REFERENCE TO RELATED APPLICATIONS

This application claims benefit of no related applications.

TECHNICAL FIELD OF THE INVENTION

This invention generally relates to an improvement in the measurement of the transit time of an ultrasonic wave through a fluid. More particularly, embodiments of the invention relate to an algorithm allowing determination of the transit time in the presence of noise and dispersion.

BACKGROUND OF THE INVENTION

In many fields use has been made of the measurement of the transit time for an ultrasonic wave through a fluid. This measurement determines the properties, flow or position of the fluids (liquid, gas, or particulate) through which the wave travels, or the location of bodies in the fluid distorting the flow of that waveform. The transit time must be measured to a high degree of accuracy and resolution. This has been done either by measuring the phase angle of the received wave compared to the phase angle of the transmitted wave, by measuring the time-of-flight of a wave packet, or by determining the peak of the cross-correlation with the transmitted wave.

The measurement of the phase angle difference between the transmitted and received signals, as by synchronous demodulation, has several drawbacks. The accurate resolution of the phase angle requires the use of a high frequency signal with a short period. It then becomes difficult to account for the number of integral periods between the transmitted and received signals since displacing the signal by one period will give the same response when the phase is measured. For a digital determination of the phase, a measurement significantly higher than the Nyquist frequency is often employed, which increases the required computational power in digital measurements. In addition, if multiple paths for the ultrasonic signal are present, they will combine at the receiver as a single frequency signal with a phase angle shift representing an inseparable contribution from each path. A phase measurement has an advantage in that a single frequency signal is commonly used and the accurate filtering of the received signal allows a large rejection of off-frequency noise.

A time-of-flight measurement modulates the envelope of the transmitted wave into a packet and detects the arrival of the packet at the receiver. The packet represents an increase of the bandwidth of the transmitted wave to roughly the inverse of the packet width. This requires a larger bandwidth in the filter of the received packet and requires an increase in the transmitted packet energy when noise is present due to increased noise passing through the input filter. Often there are multiple waveform paths slightly differing from the unperturbed waveform caused by inhomogeneous media, turbulence in the media or reflections. This uncontrollably broadens a pulse and makes the time-of-flight measurement prone to inaccuracies. Usually the determination of the arrival of the variably attenuated envelope is too imprecise to obtain an accurate transit time, so additional measurements are made on the carrier waveform using the packet arrival as a gating mechanism. This, in turn requires a high rate of data measurements and significant computations. Often these systems average over many measurements in order to improve the accuracy and resolution.

A common problem to both phase measurements and time-of-flight measurements is the nature of noise encountered in fluid measurements. Often the noise is generated by the disruptions to the fluid flow, giving rise to a "whistle" noise generation. This noise is concentrated at particular frequencies that vary with the flow rate and flow conditions as opposed to a wider bandwidth "white" noise. The measured signal can be severely affected when the noise is in the region of the measured frequencies.

In an attempt to reduce the influence of this noise, use has been made of the cross-correlation of the launched waveform and the detected waveform. U.S. Pat. No. 4,576,047 and U.S. Pat. No. 4,576,047 describe attempts to use the peak of the correlation waveform as an indication of the transit time in such a manner.

There are two principle problems encountered in attempts to measure the transit time using the methods of the prior art: the accurate determination of the transit time in the presence of noise, and the effects of dispersion on the measurement. The effects of the noise have been addressed in phase and time-of-flight measurements by increasing the power of the transmitted pulse to improve the signal-to-noise ratio. The noise is more successfully attacked by utilizing the cross-correlation between the received and transmitted waveforms. A properly chosen launched waveform has little cross-correlation with anticipated noise. The effects of dispersion in the measurements have not been generally addressed in the prior art.

There can be several causes of dispersions in the measurement of the transit time. Inhomogeneous media, where there are fluctuations in the composition or pressure of a fluid, or turbulence in the media can cause fluctuations in the velocity of sound across the transmit path causing a transmitted pulse to spread, in effect "smearing" the arrival time. A similar smearing of the arrival time is present if the media velocity is non-uniform in time, e.g. if there are "surges" in the flow. In this case, if the measurement is averaged over longer times to reduce the noise, as is done in phase measurements or cross-correlation measurements, the accelerating or deceleration appears as dispersion in the final measurement. In the case of time-of-flight measurements in such a condition the measurement is a "snapshot" in time and must be repeated often enough to obtain a statistical mean of the transit time. The aforementioned effects can be exacerbated with an increase in flow velocity in fluids, particularly gasses. The effect can be expected to depend on such parameters as average velocity, wall condition, angle to the flow path, and flow profile. There can be a systematic bias in the transit time measurements due to dispersion effects, e.g. the spread of the pulse leading edge can cause a time-of-flight measurement to indicate an early detection of a pulse compared to the pulse center.

SUMMARY OF THE INVENTION

To address these problems this invention proposes that the transmitting ultrasonic transducer be excited with a frequency-modulated signal and the signal from the receiving transducer be appropriately digitized. A reference waveform is created utilizing either the transmitted waveform, a calculation of the expected received waveform, or a measurement of the received waveform under reference conditions. The square of the convolution of the reference waveform with the received waveform is created. This calculation can be further simplified by undersampling the received signal. The squared convolution is normalized to unity area and the time-weighted average of this normalized function is summed over the proper region to give the transit time. Algorithms are presented for this calculation.

The summation can be either over minimums in the squared convolution envelope or between the minimums about the highest peak. In the latter case if the measurements are appropriately spaced a minimum number of calculations will still give a very accurate result. The region over which the summation is made is determined by the symmetry of the squared convolution in the vicinity of the peak to be considered. If there is insufficient symmetry to indicate that the measurement will be accurate, the fundamental frequency of the frequency-modulated signal may be reduced or deconvolution may be used to separate the composite signals. The former case is useful where the dispersion is asymmetric.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

In order to address the deficiencies in the measurement of the transit time in the prior art, it is proposed to transmit a source signal with a time-varying frequency content and utilize the added information in the frequency modulation to enhance the accuracy, noise rejection, and knowledge of the media through which the wave travels. If an ultrasonic waveform described by x(t) is launched into a fluid and is measured as y(t) at a later time T and different position, it is well known in the prior art that $$y(t)=\int x(\tau-t)h(\tau)d\tau=(x*h)(t) \qquad \text{(eqn. 1)}$$

where h(t) is the impulse response function and the symbol '*' represents the convolution function. This convolution is often referred to as the cross correlation. Where Y($\omega$), X($\omega$) and H($\omega$) represent the Fourier transforms of y(t), x(t) and h(t) respectively, then $$Y(\omega)=X(\omega)\cdot H(\omega). \qquad \text{(eqn. 2)}$$

For a simple media with no reflections, $$H(w)=e^{-\beta-j\omega T}, \qquad \text{(eqn. 3)}$$

or in the time domain $$y(t)=e^{-\beta}\cdot x(t-T), \qquad \text{(eqn. 4)}$$

i.e. the received waveform is an attenuated, delayed copy of the launched waveform. The convolution (x*y)(t) is given by $$(x*y)(t) = \int x(\tau-t)y(\tau)d\tau \approx \sum_{\tau} x(\tau-t)y(\tau) \qquad \text{(eqn. 5)}$$

must have a maximum at t=T for this simple case. A simple measurement of the peak will determine the transit time T and has the advantage over phase measurements and time-of-flight in that there is little likelihood of a whole period error if the signal is frequency modulated.

For the case of a transfer function given by eqn. 3 (x*y)(t) around t=T must be symmetric, i.e. (x*y)(T+t)=(x*y)(T−t), and therefore $$\int \tau\cdot[(x*y)(\tau)]^2 d\tau = T\cdot\int[(x*y)(\tau)]^2 d\tau \qquad \text{(eqn. 6)}$$

This gives a means to calculate the transit time of the signal, $$T = \frac{\int t\cdot[(x*y)(\tau)]^2 d\tau}{\int[(x*y)(\tau)]^2 d\tau} \approx \frac{\sum_t t\cdot\left[\sum_\tau x(\tau-t)\cdot y(\tau)\right]^2}{\sum_t \left[\sum_\tau x(\tau-t)\cdot y(\tau)\right]^2}. \qquad \text{(eqn. 7)}$$

If there is a symmetric distribution of the convolution about a mean, then eqn. 7 will correctly calculate this mean transit time. Where the convolution is asymmetric, this is indicative of dispersion resulting in amplitude-weighted arrival times unequally distributed around the mean arrival time that must be evaluated using deconvolution as will be described later. Equation 7 can be interpreted as generating a local normalized probability function of transit times and calculating the expected transit time from this probability.

Figure 4:
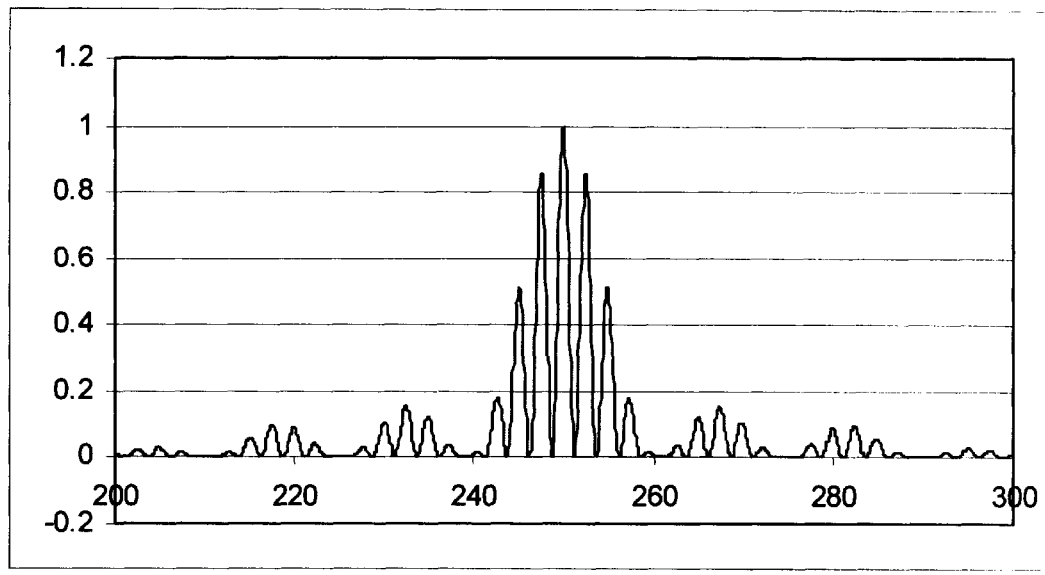
FIG. 4 shows the square of the waveform of FIG. 3. The mean arrival time calculated from this waveform is 249.9957 microseconds.
Figure 6:
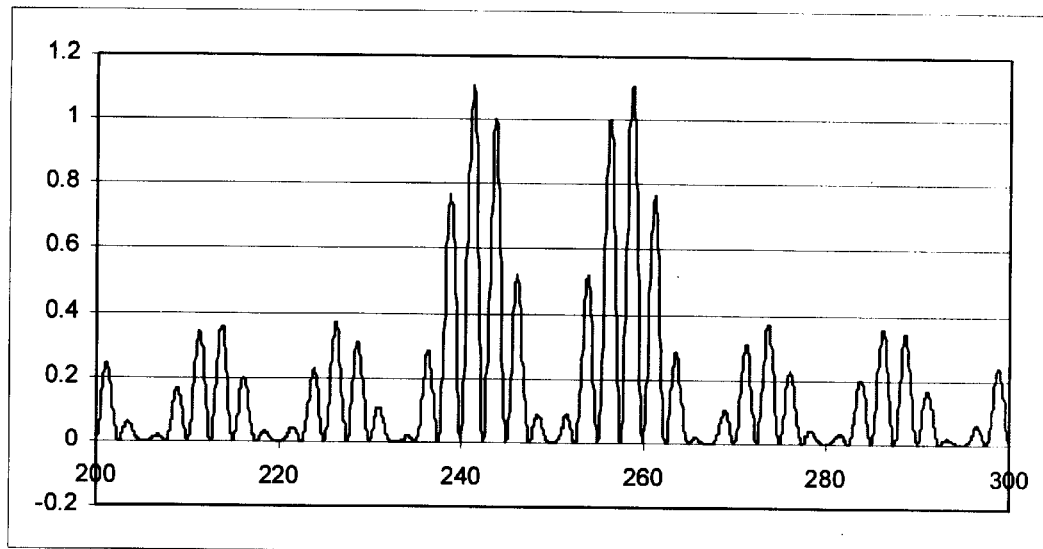
FIG. 6 shows the square of the waveform of FIG. 5. The mean arrival time calculated from this waveform is 250.0013 microseconds.

The generalized shape of the square of the convolution in the denominator of eqn. 7 is as shown in FIG. 4. The summation in equation 7 should take place between minimums of this waveform symmetric about the true value. This can be either over all points between a minimum of the envelope, or alternatively over the peak wave. Summation between minimums of the envelope is a useful technique when there are multiple peaks, as in FIG. 6. In the more general case illustrated in FIG. 4 the summation can be over the central peak.

Figure 3:
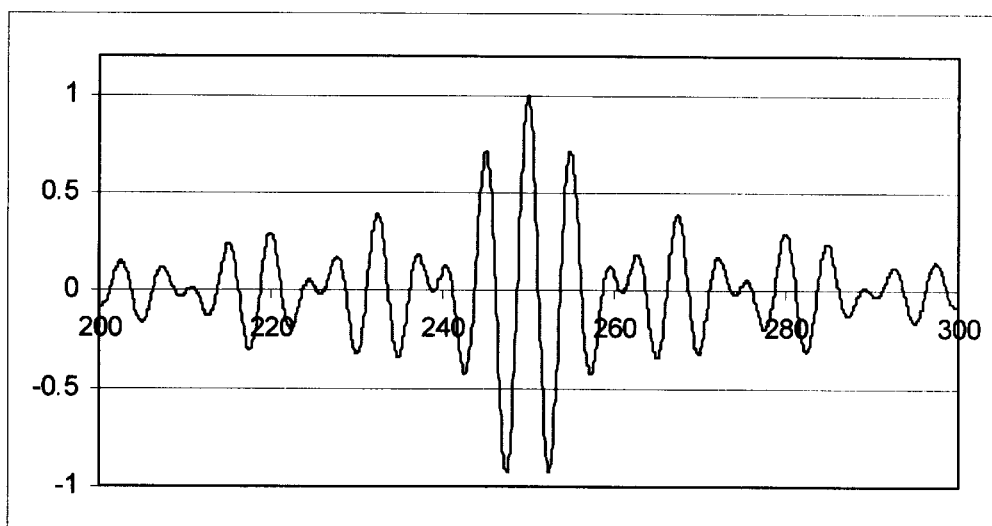
FIG. 3 shows a computer simulation of the normalized convolution of a waveform with a pulse width of 100 milliseconds, a 200 KHz base frequency sinusoidally modulated ±36 KHz. at a modulation frequency of 100 Hz. This example fixed the transit time at 250 microseconds.

Summation over a central peak can take advantage of several features of practical importance. Since the general shape of the convolution is a sinc-modulated cosine wave, the shape around the central peak of FIG. 3 is that of a cosine. The central peak in FIG. 4 is therefore in the shape of a cosine squared. It can therefore be shown that the summation of eqn 7 can be over the central peak between the points at which FIG. 3 changes sign. Since this is over an interval of $1/(2\cdot f_0)$ the interval can be fixed in time. Additionally, for any N>0 and for any $\delta$ $$\sum_{-N+1}^{N} \cos^2[(n\cdot\pi/N)+\delta] = \frac{N}{2}, \text{ and} \qquad \text{(eqn. 8)}$$

$$\sum_{-N+1}^{N} (n+T)\cdot\cos^2[(n\cdot\pi/N)+\delta] = \frac{N}{2}\cdot T. \qquad \text{(eqn. 9)}$$

This implies that the summation in equation could be carried out with N points equally spaced at $1/(2\cdot N\cdot f_0)$.

A convenient algorithm for determining the transit time in simple systems of the form where there is a central peak in the convolution of the form of FIG. 3 would be to perform convolutions at t values equally separated by $1/(2\cdot N\cdot f_0)$ by repeated applications of eqn. 5 with, giving $(x*y)_n$ and $(x*y)_n^2$. The maximum of a running sum of $(x*y)_n$ over N values can be used to find the maximum of FIG. 3 and the transit time T can be found by eqn 7 over those N values. This procedure is illustrated in the flow chart of FIG. 19. The effect of N on several calculations using the algorithm in FIG. 19 are as follows for a transit time of 250 microseconds:

| N | T |
|---|---|
| 2 | 249.999730 |
| 3 | 249.998402 |
| 4 | 249.999362 |
| 5 | 249.999021 |
| 6 | 249.999308 |
| 8 | 249.999294 |
| 10 | 249.999273 |

Figure 5:
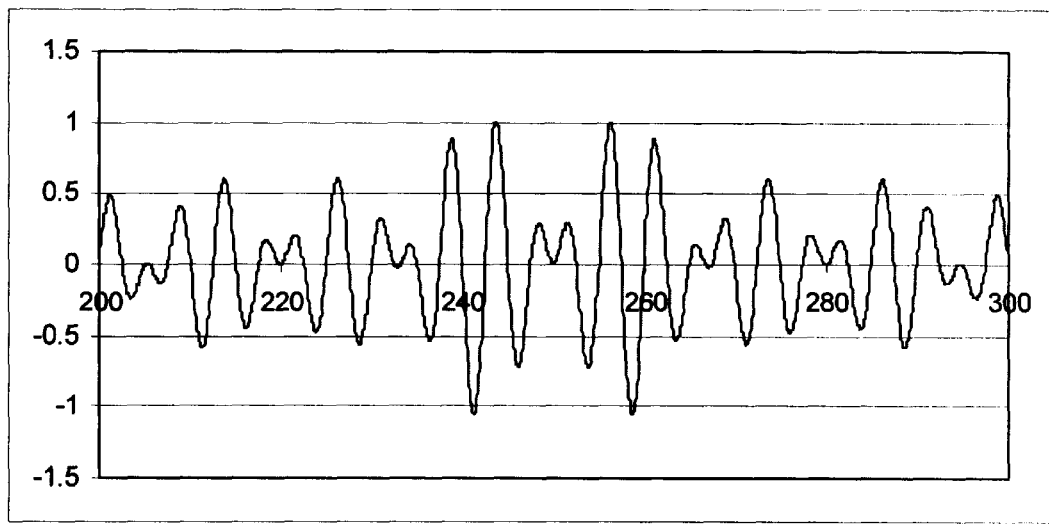
FIG. 5 shows a computer simulation of the normalized convolution of a sinusoidal modulated waveform with a pulse width of 100 milliseconds, a 200 KHz base frequency modulated ±36 KHz. at a modulation frequency of 100 Hz. A worst-case signal dispersion case is shown where two equal amplitude signals arriving with transit times of 248.75 microseconds and 251.25 microseconds, i.e. arriving 180° of the base frequency out of phase.
Figure 19:
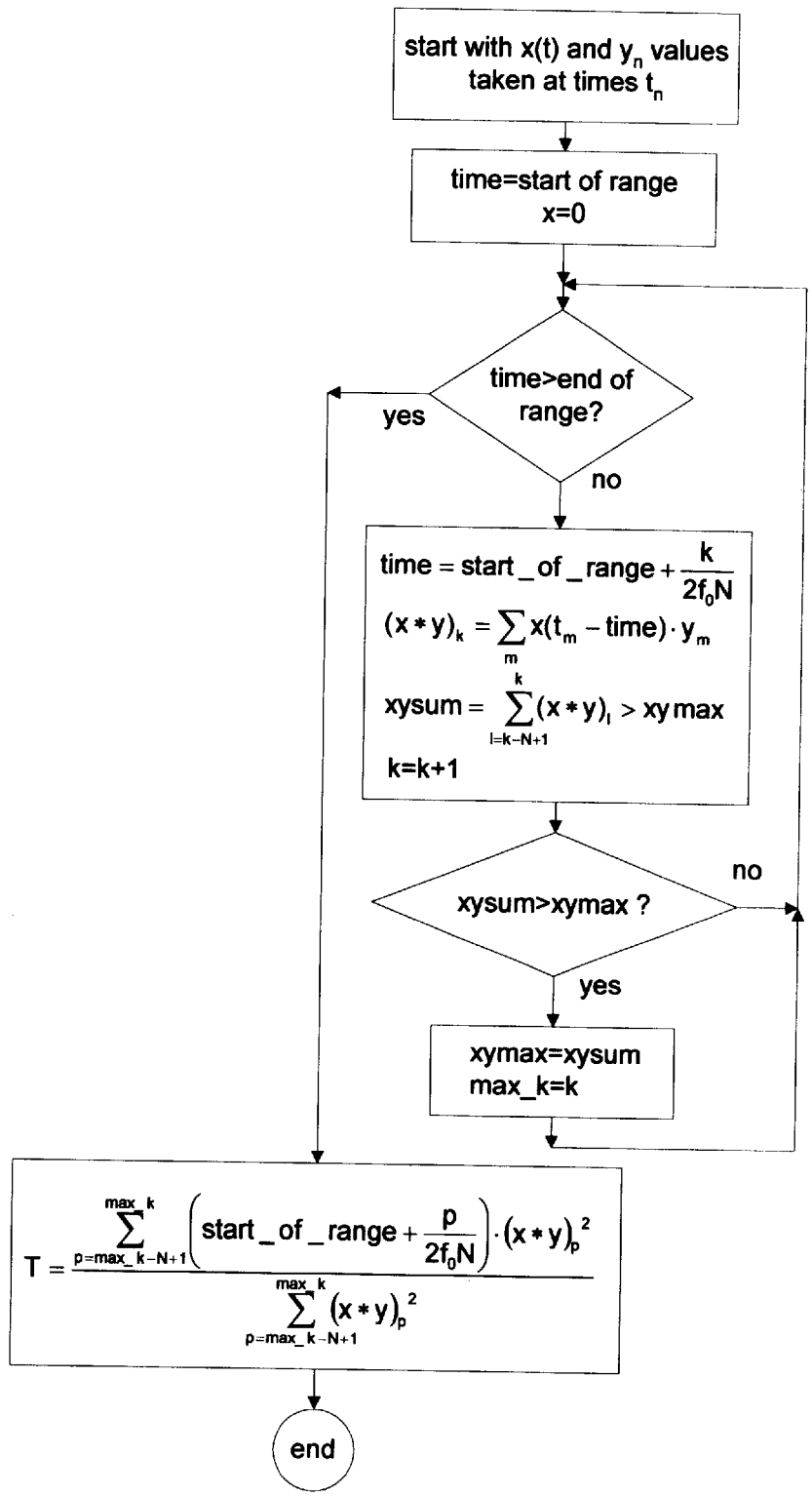
FIG. 19 illustrated a flow diagram for one implementation of the method presented for the calculation of the transit time.

The accuracy that can be achieved by the flow chart of FIG. 19 allows a further modification. In many cases in the prior art the frequency $f_0$ utilized in ultrasonic measurements has been increased in order to improve the accuracy of the time resolution. A fixed amount of time dispersion is then moved into adjacent side lobes, moving and distorting both the original peak and the symmetry in a nonlinear fashion. FIG. 5 will be shown to present two equal waves whose arrival times are centered at 250 microseconds and spaced 1.25 microseconds apart. The situation is further complicated where the weighting of the two waves is unequal, and any simple analysis has been difficult. This situation is not a problem for slight deviations from the main peak, where the two cosine functions combine to a phase shift of the cosine that is a weighted sum of the component cosine waves. The accuracy of the calculation using the algorithm of FIG. 19 allows a reduction in $f_0$ to a value that could include all expected dispersion within the maximum correlation peak. For example, if a wave with $f_0$ value of 20,000 Hz. was used to analyze the effect of a wave arriving at 250 microseconds with an amplitude of one and a simultaneous wave of varying amplitude arriving at 253 microseconds. The values calculated for ratios of the second wave were as shown in the following table:

| Weight of 253 usec wave relative to 250 usec wave | (250) + column_1·(253) / 1 + column_1 | Transit time calculated from FIG. 19 algorithm |
| --- | --- | --- |
| 0 | 250.0000 | 249.9993 |
| 0.1 | 250.2727 | 250.2641 |
| 0.2 | 250.5000 | 250.4890 |
| 0.3 | 250.6923 | 250.6816 |
| 0.4 | 250.8571 | 250.8477 |
| 0.5 | 251.0000 | 250.9922 |
| 0.6 | 251.1250 | 251.1187 |
| 0.7 | 251.2353 | 251.2303 |
| 0.8 | 251.3333 | 251.3295 |
| 0.9 | 251.4211 | 251.4186 |
| 1 | 251.5000 | 251.4989 |

The use of a lower frequency $f_0$ in the frequency-modulated source function to obtain an averaged transit time raises the possibility of flooding the entire cross-sectional area of the pipe with the lower frequency ultrasonic signal and using this property to average out the flow profile and swirl in the measurement of a fluid flow. Analyzing the symmetry of the correlation function about the peak can show the need for some technique for accommodating dispersion. If this waveform is asymmetric, any calculation on the peak is affected by conditions outside the peak.

It is to be understood that this analysis is in terms of a convolution in time and frequency space and with a Fourier transform, but equivalent operations using other spaces and transforms may be used. Examples of other equivalent evaluations would be the convolution utilizing Z transforms or the various convolution equivalents utilizing wavelets. This invention is phrased in terms of the more conventional ultrasonic waves, but it is to be understood that the discussion is more general, and of equal application to other wave phenomena, such as sonic waves.

As the modulation information, rather than the base frequency, contains the distinguishing information, techniques such as the undersampling of the received signal can be utilized to significantly reduce the calculations involved. This wave is equivalent to using the lower side lobe and is the mathematical equivalent of heterodyne demodulation followed by low pass filtering, which would also reduce the necessity of taking measurements at greater than the Nyquist frequency.

There are many possible forms for the exciting function, with possibilities for the envelope, the frequency modulation scheme (which is incorporated in the envelope function), $f_0$, and pulse width. The choice depends on such factors as the dispersion expected, the noise expected, and the hardware. In using the algorithm of FIG. 19 a measure of the strength of the received signal is given by the denominator of eqn. 7, or in the algorithm of FIG. 19, the $$\sum_{p=index-N+1}^{index} (x*y)_p^2$$

term in the calculation. A measure of the correlated noise can be found in such a system by performing the calculation without applying the excitation to the output transducer, and comparing the unexcited strength of this value with the strength with excitation. If the unexcited figure is too high, a different excitation can be interactively incorporated until this figure is sufficiently reduced for the accuracy required in a particular application.

Figure 1:
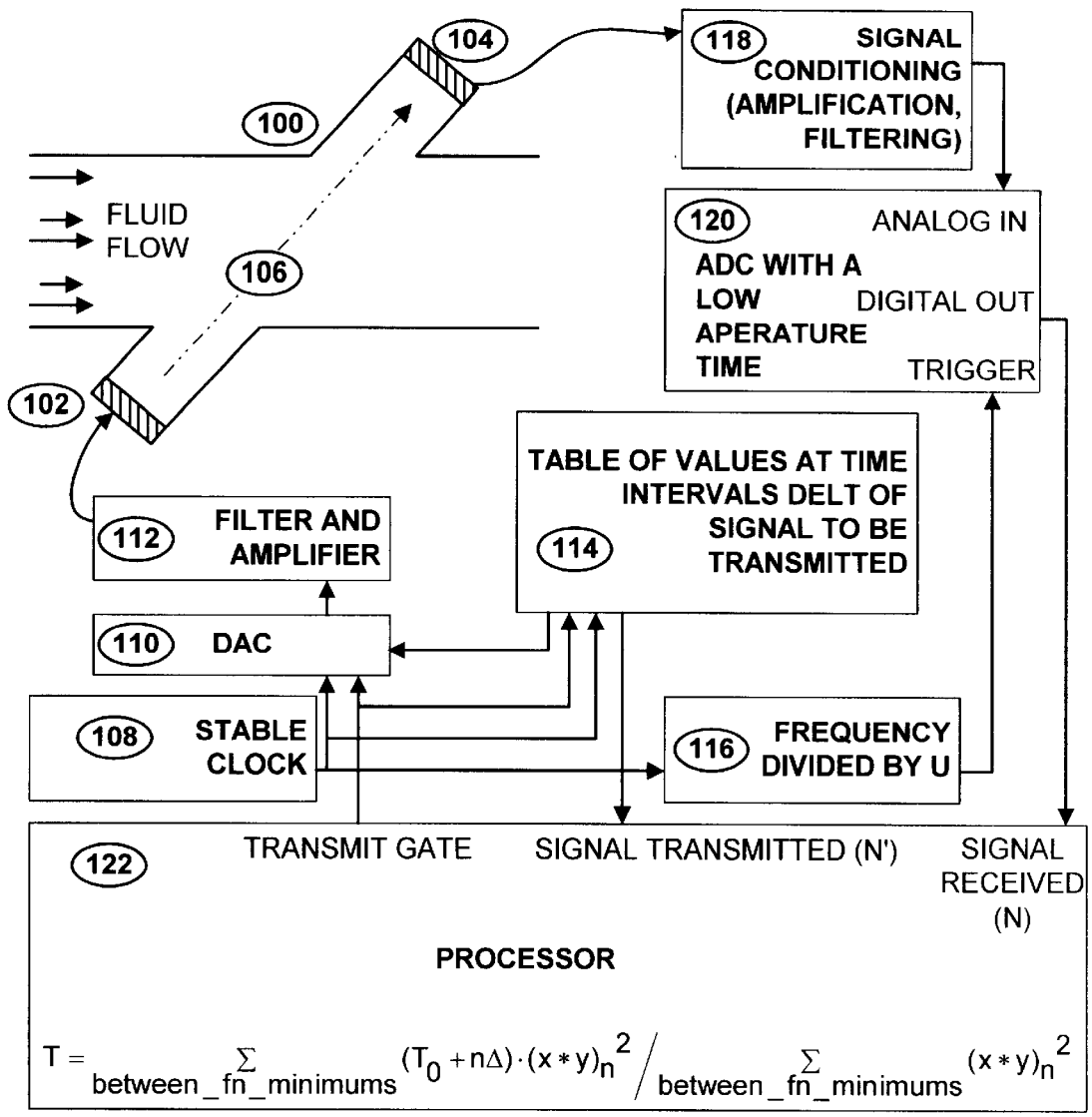
FIG. 1 shows a high-level block diagram of an embodiment of a ultrasonic measurement system. An ultrasonic waveform representing a frequency-modulated signal is synthesized from a stored table of values and launched from an ultrasonic transducer into the fluid whose velocity is to be measured. The waveform received at the opposite ultrasonic transducer is digitized at a much lower frequency and a processor calculates the convolution of the received waveform and a reference waveform.

An exemplary configuration of an ultrasonic measurement system is illustrated in FIG. 1. A common arrangement for ultrasonic transducers used to measure fluid flow in a pipe is illustrated. The pipe 100 has an oblique mounting for two ultrasonic transducers 102 and 104. In the example shown transducer 102 is functioning as a transmitter to send an ultrasonic wave 106 to ultrasonic transducer 104 that converts the received wave to an electronic signal. This wave will be referred to as the forward wave. Commonly the action is then reversed and transducer 104 launches an ultrasonic wave in the opposite direction to that illustrated by 106 and transducer 102 converts the received waveform to an electronic signal. This wave will be referred to as the reverse wave. It is to be understood that the following discussion describing the forward wave can be applied to the reversed wave measurement by the duplication of the electronics or by mechanically or electronically exchanging the connections to 102 and 104. The rate of flow is determined by methods well known in the prior art by use of the transit times for the forward and reverse waves.

Figure 2:
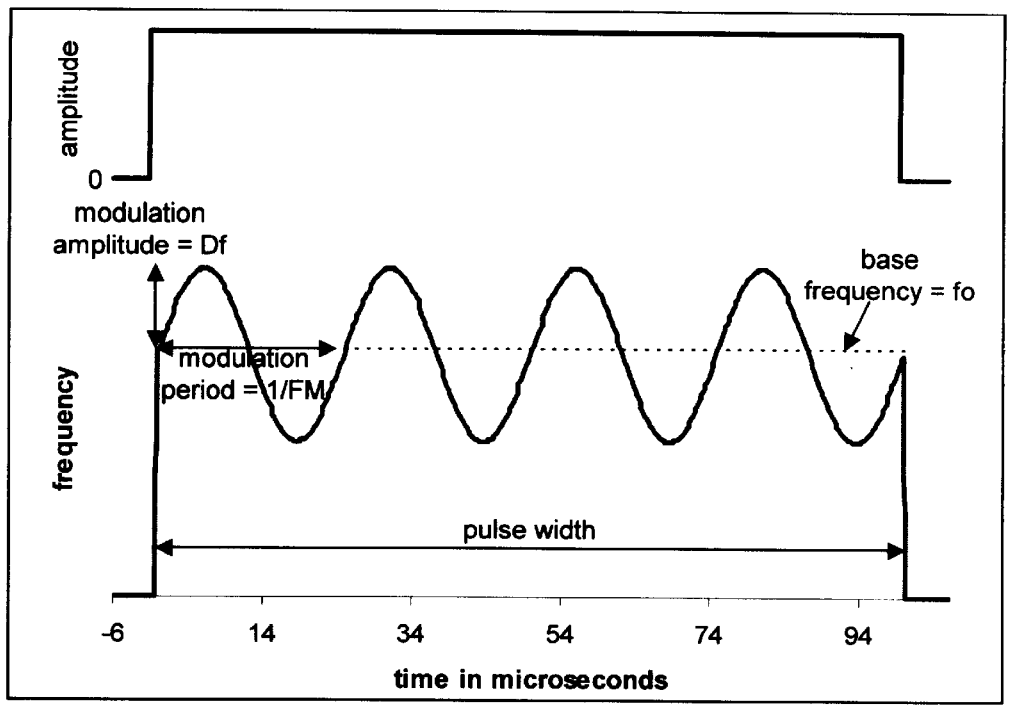
FIG. 2 shows one embodiment of the frequency modulation whereby the frequency rises to a level centered about a base frequency $f_0$. This frequency is then modulated at a modulation frequency FM above and below the base frequency by an amount Df. At the end of the pulse width the amplitude is reduced to zero and the pulse ends.

The transmitter 102 generates an ultrasonic waveform 106 that passes through the fluid to be measured and is detected by the receiver 104. In a particular embodiment the transducers 102 and 103 can be excited by a frequency modulated signal of the form $$\text{transmit\_signal}(t) = A \cdot \sin[\omega(t) \cdot t] \quad 0 < t < \text{pulse width} \quad \text{(eqn. 10)}$$
$$= 0 \quad \text{elsewhere}$$

$$\text{where } \omega(t) = 2 \cdot \pi \cdot \left[ f_{0+} + \frac{2DF}{2 \cdot \pi \cdot f_m} \cos(2 \cdot \pi \cdot f_m t) \right] \quad \text{(eqn. 11)}$$

and Df is the range of the frequency deviation from the fundamental frequency, $f_0$, and $f_m$ is the modulation frequency. This is a sinusoidal modulated frequency pulse 100 milliseconds wide with an instantaneous frequency varying above and below $f_0$ by an amount Df at a frequency $f_m$. The shape of the waveform is as shown in FIG. 2 for a pulse width of 100 milliseconds. It is understood that this is one example of many possible frequency-modulated signals as eqn. 7 is applicable for a generalized waveform.

After this waveform is launched from transmitter 102, if there are no multiple paths it will arrive at the receiver 104 after a transit time T. The received signal with a signal attenuation B is $$\text{receive\_signal}(t) = A \cdot B \cdot \sin[\omega(t-T) \cdot (t-T)] \quad T < t < T + \text{pulse width} \quad \text{(eqn. 12)}$$
$$= 0 \quad \text{elsewhere}$$

$$\text{where } \omega(t-T) = 2 \cdot \pi \cdot \left[ f_{0+} + \frac{2DF}{2 \cdot \pi \cdot f_m} \cos(2 \cdot \pi \cdot f_m \cdot (t-T)) \right]. \quad \text{(eqn. 13)}$$

The desired intermediate signal generated by processor 122 will be $$(x*y)_n = \sum_\tau [\text{transmit\_signal}(\tau - t) \cdot \text{receive\_signal}(\tau)] \quad \text{(eqn. 14)}$$

In the example shown in FIG. 1 the waveform of the shape of eqn. 10 can be stored in memory 114. When the waveform is to be launched processor 122 gates the memory so that the sequence of values is fed to the DAC 110 at a rate determined by stable clock 108 triggering the conversion of these values to an analog waveform. This waveform is filtered to reduce the harmonics introduced by quantization, amplified and applied to the ultrasonic transmitter 102.

The receiving ultrasonic transducer 104 converts the received waveform to an electronic signal that is filtered for out-of-band frequencies by the preamplifier 118. The stable clock 108 is divided by a factor U in the divider 116 to generate a much lower sampling frequency that is used to trigger the digitization of the received signal by a low aperture time analog-to-digital converter 120. This converts the received signal to a series of undersampled digital values that are fed to processor 122, which can be a dedicated microprocessor or an appropriately programmed general-purpose computer. In the computer simulations to be described the data was taken at a 20 microsecond rate, i.e. 5005 readings for a 100 millisecond pulse width or 505 readings for a 10 millisecond pulse width. This gives coverage of a 100 microsecond time range. Within this range, if the algorithm of FIG. 19 is calculated with N equal to 8, there will be 320 summations of the data readings. Where the processor is calculation-limited, a N can be reduced.

This processor 122 has either knowledge of, or is the generator of the signal output waveform table 114, together with the digitized values of the received signal. For the exemplary configuration, N=8 and there is a pulse width of 100 milliseconds, a fundamental frequency $f_0$ of 200 KHz, a modulation frequency $f_m$ of 100 Hz. and a modulation amplitude of Df of 36 KHz. Table 114 stores 320,000 values, implying that the clock frequency of 108 would be 3.2 megahertz. The values fed to DAC 110 at this $f_0$ represent about 16 values per output cycle. If ADC 120 receives trigger pulses from 116 at a rate of 50 KHz, frequency divider 116 would divide the input by a factor of 64.

In order to satisfy the intrinsic safety issues often encountered in pipeline measurements, processor 122 can be split. A limited local processor can gate the measurements stored in a local RAM or ROM 114, and transfer the relatively low bandwidth measurements to a remote, safe-area processor for the intensive calculations. For the example just described, for measuring the wave arrival in a 100 microsecond window, 5005 values in the forward direction and 5005 values in the reverse direction would be sent for a measurement, with a measurement taking less than one-quarter second. This would give four readings per second with an intercommunications bandwidth of about 88 Kbaud. If the pulse width is reduced to 10 milliseconds the four readings would require 8.8 KBaud. As will be seen, each reading is extremely noise immune and there is little loss in accuracy with a 10 millisecond pulse width so the lower frequency is quite feasible.

FIG. 3 illustrates the normalized result of such a calculation for a simple wave of the form of eqn. 4 with a range of interest between 200 and 300 microseconds and a delay time T=250 microseconds. FIG. 4 illustrates the shape of $(x*y)_n^2$. If the algorithm of FIG. 19 is applied with N=8 for the results plotted in FIG. 4, a calculated transit time of 249.9990 microseconds is obtained showing the inherent accuracy of this transit time determination. The high accuracy in the calculation of T can be attributed to the utilization of all points in the received measurement in its determination as opposed of the few points used in a time-of-flight measurement.

A worst-case example of dispersion is when the wave is split into two components separated by 180° of the measured frequency so that the waves destructively interfere. In such a case neither the phase measurement nor the time-of-flight measurement from the prior art will function. FIG. 5 shows the normalized result of two equal-amplitude signals arriving at 248.75 and 251.25 microseconds, i.e. half the $f_0$ period. The source waveform is that described previously for FIG. 3. As can be seen, there is destructive interference at T but the calculation of eqn. 16, with a $(x*y)_n$ shown in FIG. 6 between points of symmetry, e.g. between minimums around 233 and 267 microseconds, gives a mean transit time of 250.0013 microseconds.

Figure 7:
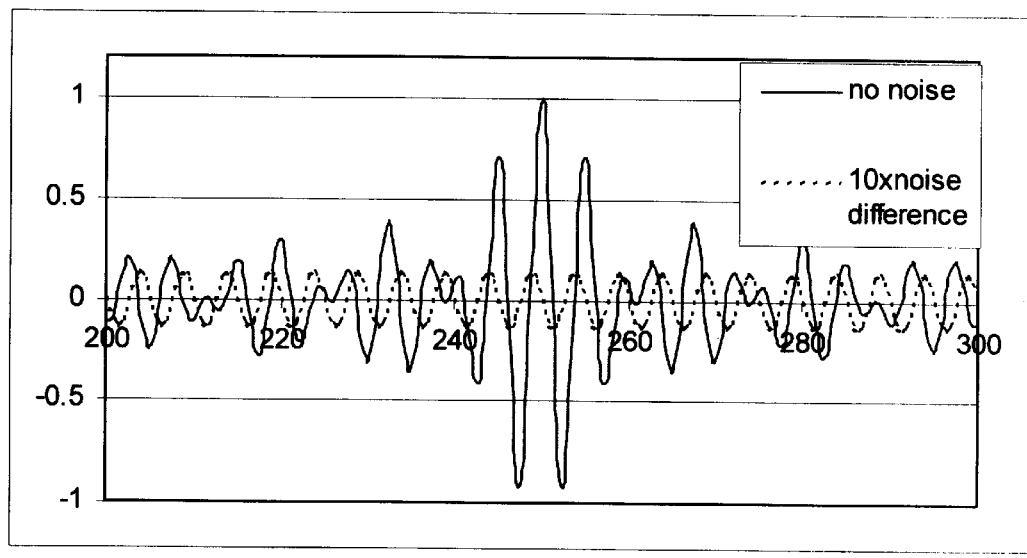
FIG. 7 shows a computer simulation of the normalized convolution of a sinusoidal modulated waveform with a pulse width of 100 milliseconds, a 200 KHz base frequency modulated ±36 KHz. at a modulation frequency of 100 Hz. A constant-frequency noise signal at 200 KHz and an amplitude equal to the received signal was added to the received signal to show the effect of a constant-frequency noise. The solid dotted line is ten times the difference between the signal with and without the noise. The signal transit time was 250 microseconds and the calculated mean arrival time was 249.9958 microseconds.

As mentioned previously, noise is a major problem in many ultrasonic measurements. To affect measurements the noise must be correlated to the source and the type of measurement. For example, a constant-frequency phase measurement is destroyed by noise at the measured frequency and a time-of-flight measurement looking for the arrival of the signal or the signal zero crossings is distorted by almost any noise. In contrast, the convolution of any well-designed frequency-modulated signal with the noise signal is minimal. As an illustration, the example described previously and shown in FIG. 3 can be combined with a noise signal at $f_0$ with the same amplitude as the received signal then FIG. 7 shows the convolution $(x*y)_n$ and 10 times the difference between the signal with noise and the signal without noise. Other modulation schemes have lower cross correlation. This noise caused a 9 nanosecond error in the calculated transit time. Multiple measurements to improve noise rejection, as is often utilized in time-of-flight measurements, are unnecessary.

Figure 8:
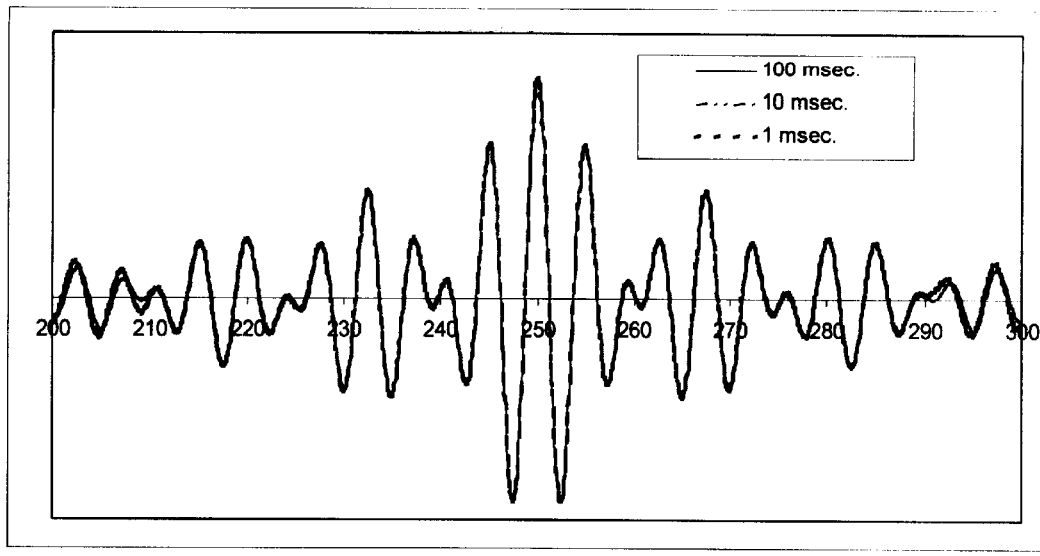
FIG. 8 shows a comparison of the waveform shown in FIG. 3 with a waveforms generated under the same conditions except the pulse width was reduced to 10 milliseconds and to 1 millisecond.

In some systems the calculations described previously may be burdensome. The measurement of the transit time described in this invention allows the use of smaller pulse widths and coarser measurements than the example cited. FIG. 8 illustrates the effect on $(x*y)_n$ of reducing the pulse width from the 100 milliseconds described previously to 10 milliseconds and to 1 millisecond. The waveform is little affected, allowing an order-of-magnitude reduction of the computing required. Proper choice of the pulse width, pulse waveform, and measurement separations can make this method of determining the transit time within the capability of inexpensive microprocessors. The noise rejection is roughly that of a filter with a bandwidth of the inverse of the pulse width, so the narrower pulse width is at the expense of noise rejection and the failure to average over possible periods of the temporal fluctuations of the measurement.

Prior art has not discussed the determination of the dispersion of the transmitted wave. This information would provide useful insight to inclusions in the media, phase separation in the media and turbulence in the media. Using the relationship described in eqn. 2 it can be shown that $$X(\omega) \cdot Y(\omega) = [X(\omega) \cdot X(\omega)] \cdot H(\omega), \quad \text{(eqn. 17)}$$

where the function in brackets is the autocorrelation of the source and the function on the left is the Fourier transform of the (x*y)(t) considered previously. As everything is known except the transfer function H($\omega$) this is a case of performing a deconvolution for which there are a number of techniques available in the literature. Use has been made of cepstrum analysis, homomorphic deconvolution, and wavelet theory. Since for simple arriving waves of the form of eqn. 4, another method of deconvolution is the iterative additions of the autocorrelation of the source function with differing arrival times and amplitudes to generate (x*y)(t). Such an approach easily leads to the resolution of the data comprising FIG. 5 into two waveforms of the shape of FIG. 3 centered at 248.75 and 251.25 microseconds.

Figure 9:
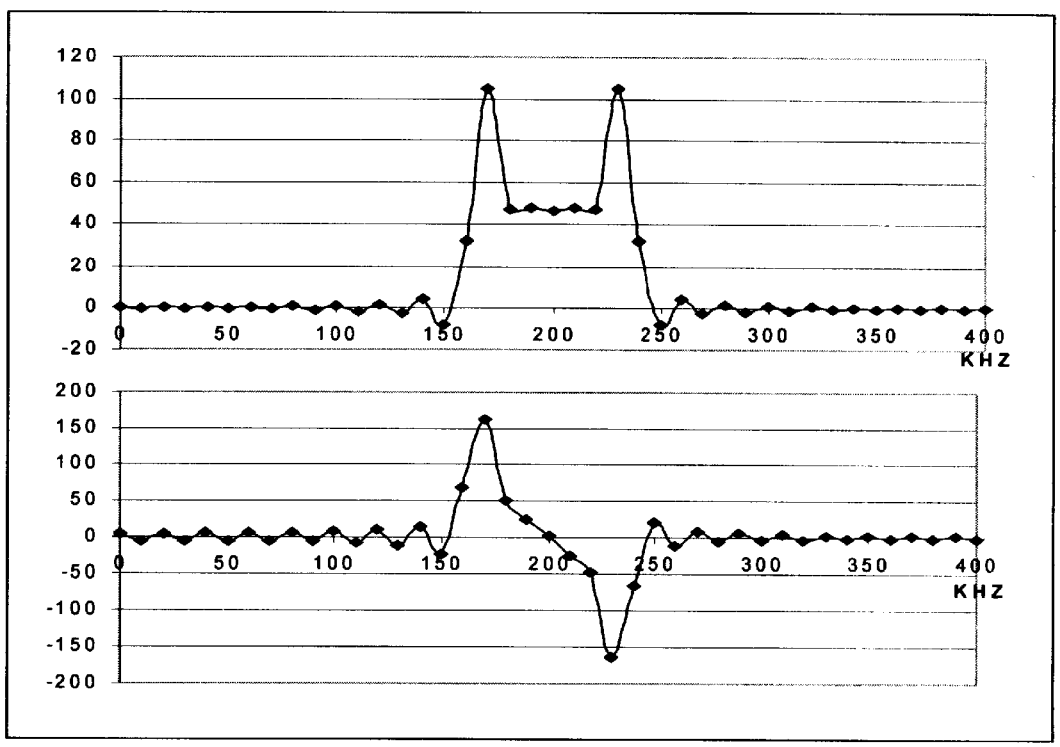
FIG. 9 shows (top) waveform the discrete Fourier transform of the time signal shown in FIG. 3 for comparison with the discrete Fourier transform of the time signal shown in FIG. 5 (bottom).

Another simple illustration of deconvolution is the case previously considered in FIG. 5 where two equal waves separated by different path lengths arrive out of phase at the receiver. In this case FIG. 9 illustrates on the top the discrete Fourier transform of the autocorrelation of the source and the bottom shows the discrete Fourier transform of the (x*y)(t) shown in FIG. 5. For the two individual paths the transform is of the form of eqn. 3 so that if attenuation is insignificantly different for the path lengths $$H(w) = e^{-\beta + j\omega(T+\theta)} + e^{-\beta + j\omega(T-\theta)} = 2e^{-\beta + jT} \cos(\omega\theta). \quad \text{(eqn. 18)}$$

Neglecting the amplitude, since the figures are normalized, and the constant delay, the autocorrelation transform should be multiplied by a real cosine, as it apparently is. From this it is evident that the zero crossing is at $\pi/2 = 2\pi(200{,}000\ Hz)$ $\theta$, or $\theta$, which is half the delay between the two paths, is 1.25 microseconds, in agreement with the 2.5 microsecond difference between the two waves creating FIG. 5. This is an illustration of the usefulness of deconvolution in determining the nature of the received signal.

The term x($\tau$-t) in eqn. 1 represents the source signal delayed by a time t. In the example given the source waveform was known and controlled. If the source waveform is not known but is repeatable, the received waveform can be measured in a reference condition, e.g. with no flow, and used as x(t) where now t represents the time relative to the measurement condition. This allows compensation for the transform through the source and receiving transducers while allowing the rejection of noise that could couple with the source waveform but not the actual waveform. Additionally, this would allow the use of naturally-occurring sources whose excitation is not controlled. The received waveform can be determined either by actual measurement or theoretically through a knowledge of the system physics. In this case all the previous analysis applies except the derived T represents the time difference between the reference condition and the measured condition and the deconvolution detects perturbations in the transfer function.

Figure 10:
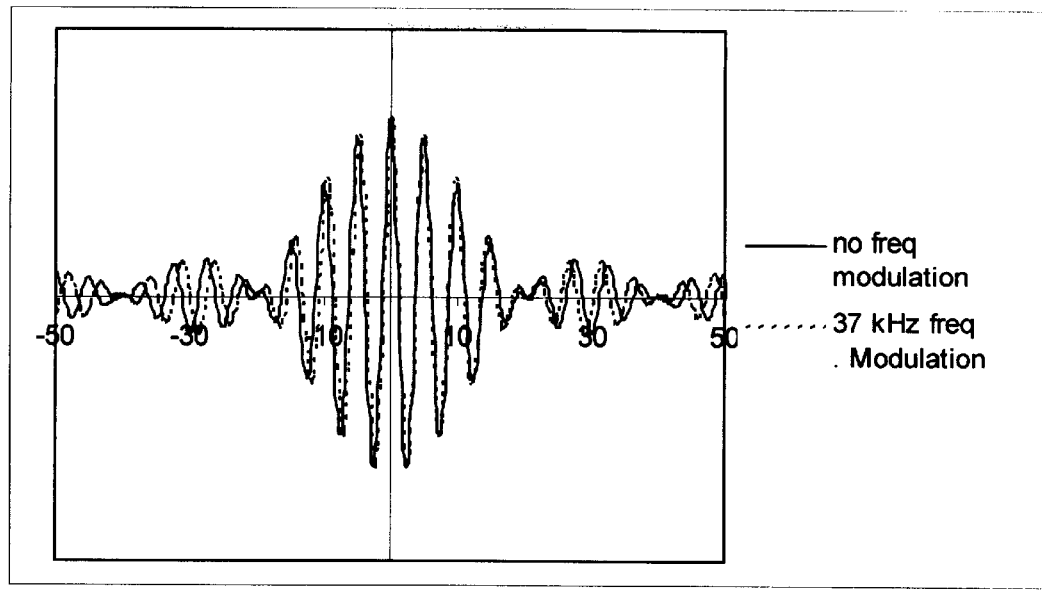
FIG. 10 shows computer simulation waveforms of a sinc amplitude-modulated waveform with and without a 37 kHz linear frequency modulation of the 200 kHz. carrier frequency.

The method utilized in the measurement of the transit time can illustrate the influence of the source signal on the noise rejection. For a simple time-of-flight measurement a source waveform can be a sinc-modulated sine wave of the form shown in FIG. 10 for a computer simulation with $F_0$ of 200 KHz. and a linear FM of 25 KHz. for the generation of the sinc function. The formula for the zero-centered sinc envelope frequency-modulated signal would be $$\text{signal\_out} = \left(\frac{\sin(2 \cdot \pi \cdot FM \cdot t)}{2\pi \cdot FM \cdot t}\right) \cdot \cos(2 \cdot \pi \cdot f_0 \cdot t) \quad \text{(eqn. 19)}$$

Figure 11:
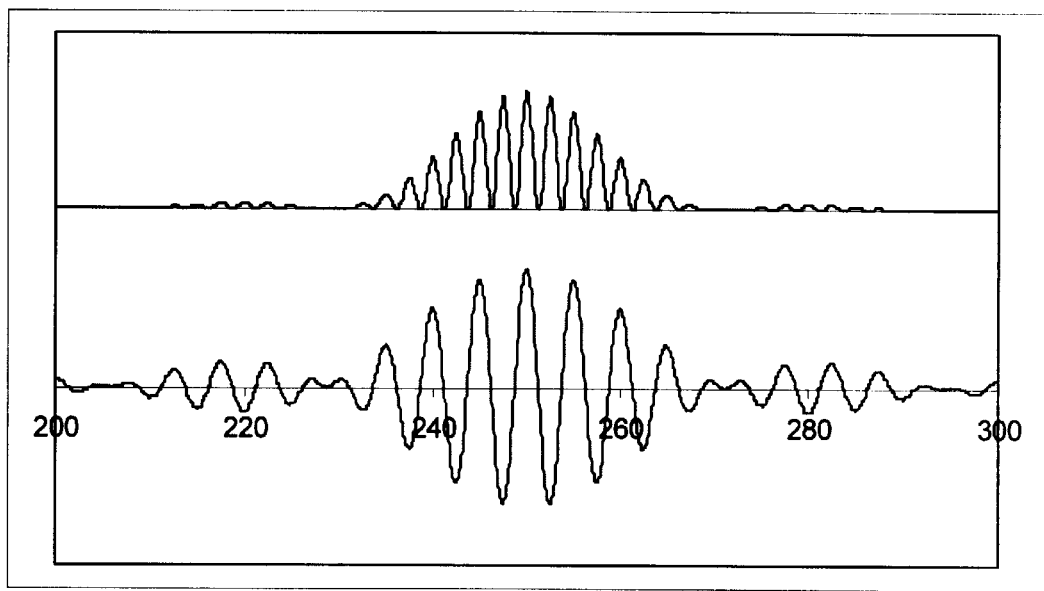
FIG. 11 shows the convolution waveform (bottom) of the sinc amplitude-modulated waveform with no frequency modulation as shown in the solid line of FIG. 10. The top waveform is the square of the convolution waveform shown in the bottom waveform.

The time of arrival of this pulse can be amplitude-gated and the time delay of the zero-crossings of the waveform further determined to gain a refinement of the measurement. Alternatively, the method of eqn. 7 can be used to determine the time of flight from the measured values convolved with the source as shown previously. FIG. 11 illustrates a computer simulation of the convolution (x*y) (bottom) and the convolution squared (top). An interval of 0.2 microseconds was used between calculated values of (x*y), as undersampling to recover the side lobe is unwarranted in such a short pulse width. From this the transit time can be determined by eqn. 7. For the example shown the calculated transit time was accurate to within nanoseconds.

Figure 12:
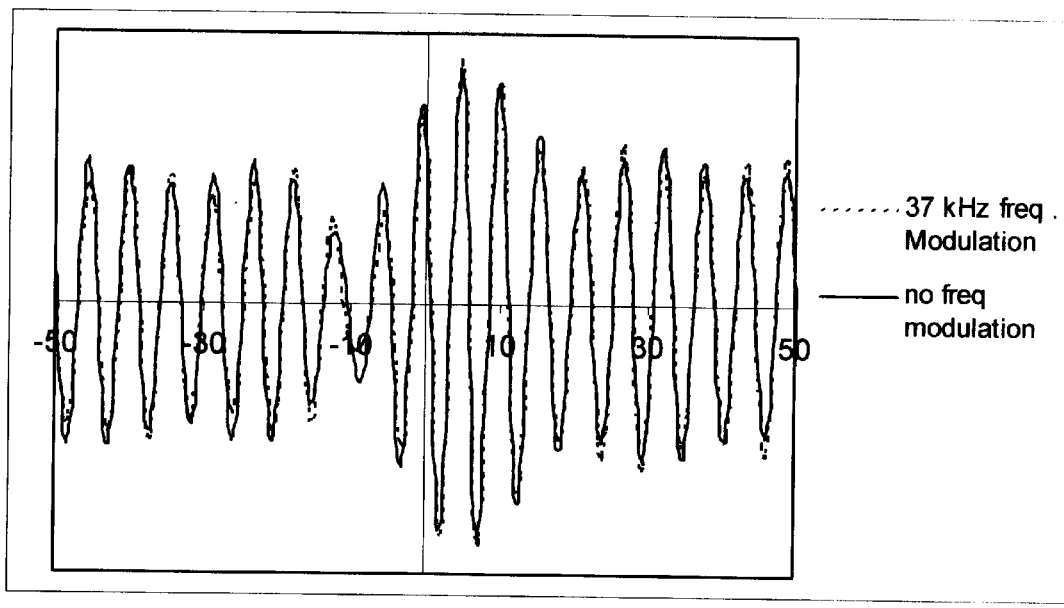
FIG. 12 shows the sinc amplitude-modulated waveforms of FIG. 10 with the addition of a noise signal at a frequency of a 180 kHz. and a phase angle of 1.25 microseconds relative to the center of the arrived sinc function.
Figure 13:
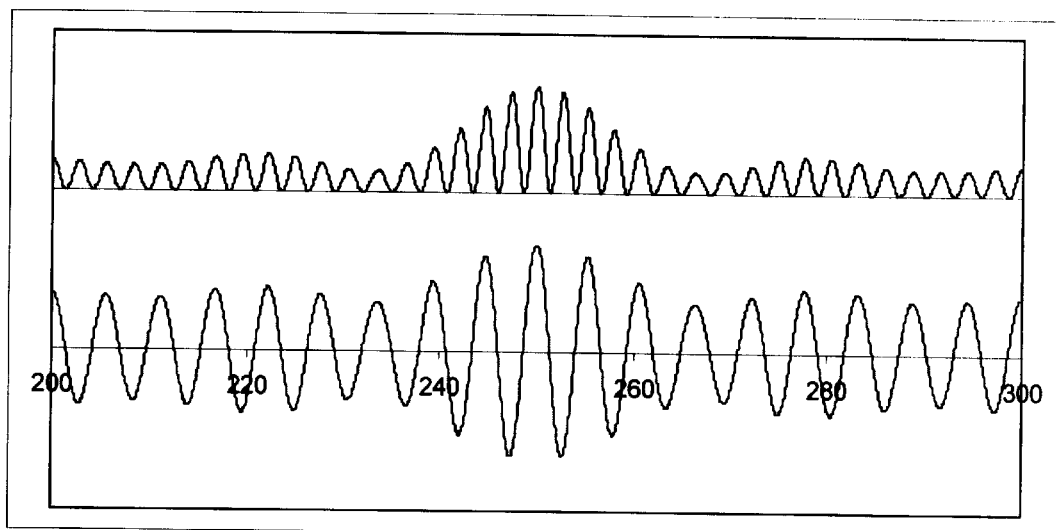
FIG. 13 (bottom) shows the convolution function of the solid line in FIG. 12, a sinc amplitude-modulated function envelope with no 200 kHz. carrier frequency modulation. The top waveform is the square of the convolution waveform shown in the bottom waveform.

Since the Fourier transform of the sinc envelope is a rectangular function from 0 to FM, and the Fourier transform of the carrier wave is a unit impulse function at $f_0$, the modulated waveform in frequency is the convolution of the two, or a rectangular function centered at $f_0$ of width 2 FM on the j$\omega$ axis. This will have a significant convolution with any noise within that frequency range. To see this, the solid line of FIG. 12 represents the signal in FIG. 10 with an additive equal-amplitude wave of a constant 180 KHz. frequency with a phase angle relative to the sinc function of 1.25 microseconds. The vertical line at t=0 represents the center of the received sinc pulse. As is evident, a heuristic algorithm for the extraction of the transit time is difficult to imagine. Application of eqn. 7 would lead to the convolution and convolution squared shown in FIG. 13. An attempt to determine the summation range in eqn. 7 from the minimum of the envelope can be seen to lead to critical decisions since, contrary to the case of FIG. 11, there is no minimum near zero where non-critical changes in the summation range can be made. The algorithm of FIG. 19 can still be applied to the main peak, although in the event this is very likely to be distorted.

A slight change can be made to the signal out:

$$\text{signal\_out} = \left(\frac{\sin(2 \cdot \pi \cdot FM \cdot t)}{2\pi \cdot FM \cdot t}\right) \cdot \cos[ \quad \text{(eqn. 20)}$$
$$2\pi \cdot f_0 \cdot (t + .37 \cdot (.01 \cdot t - (int)(.01 \cdot t + .5)) \cdot (-1)^{(int)(.01*t+.5)})]$$

Figure 14:
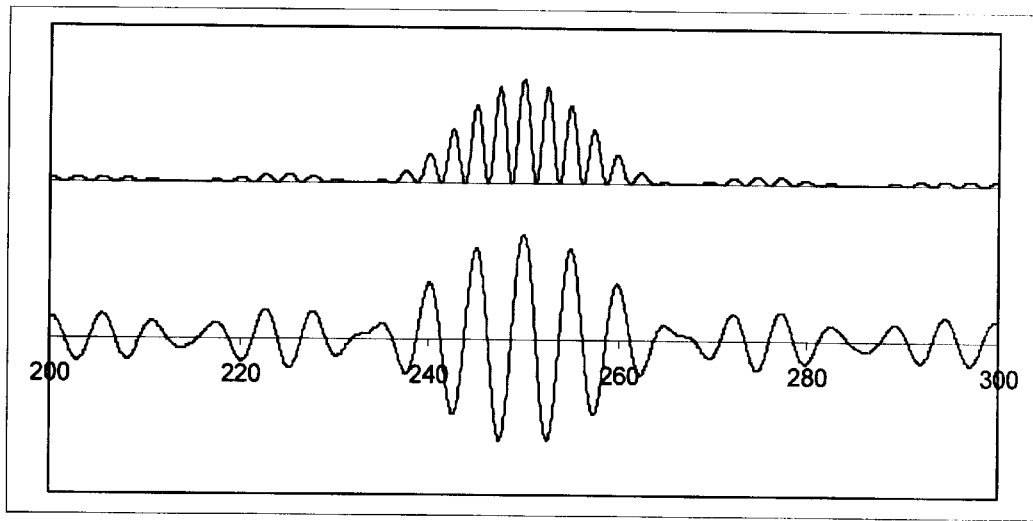
FIG. 14 (bottom) shows the convolution function of the broken line in FIG. 12, a sinc amplitude-modulated function envelope with 37 kHz. linear frequency modulation of the 200 kHz. carrier. The top waveform is the square of the convolution waveform shown in the bottom waveform.
Figure 15:
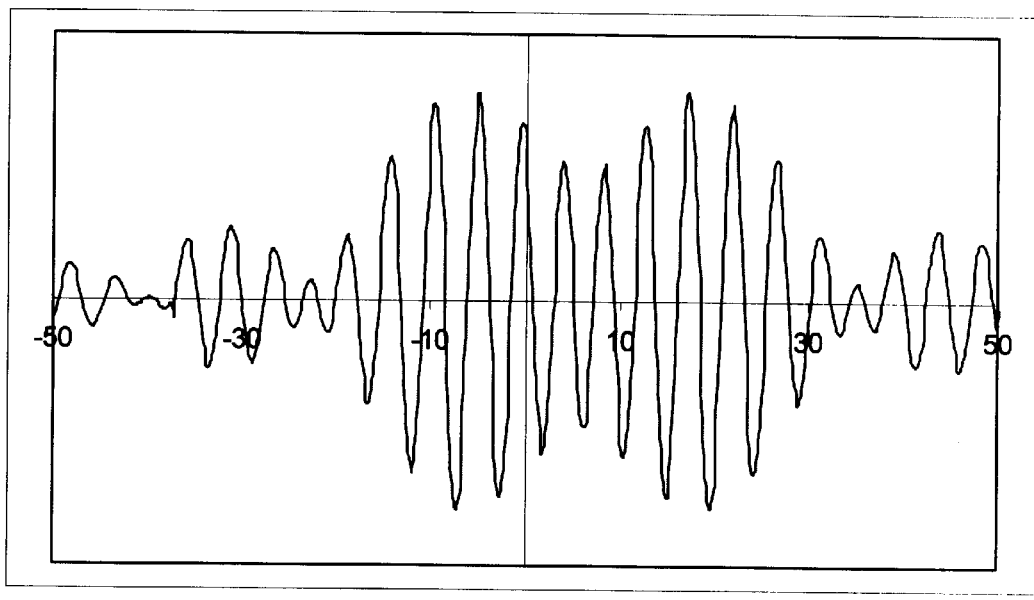
FIG. 15 shows a computer simulation of the waveform formed by two equal-amplitude sinc envelope waves with a linearly 37 kHz. frequency-modulated carrier frequency. The arrival times of these two pulses differ by 12.5 microseconds, two and one-half $f_0$ periods. The vertical line represents the center of the first sinc envelope.

The frequency is now frequency-modulated modulated by a linear term. In the time domain the signal is slightly changed as seen by the difference between the frequency-modulated signals as shown by the dotted lines in FIGS. 11 and 13. The correlation and square of the correlation can be seen for this frequency-modulated wave in FIG. 14, showing minimums about which the summation in eqn. 7 can be non-critically performed. In this computer simulation the transit time can be calculated to within 10 nanoseconds.

Figure 16:
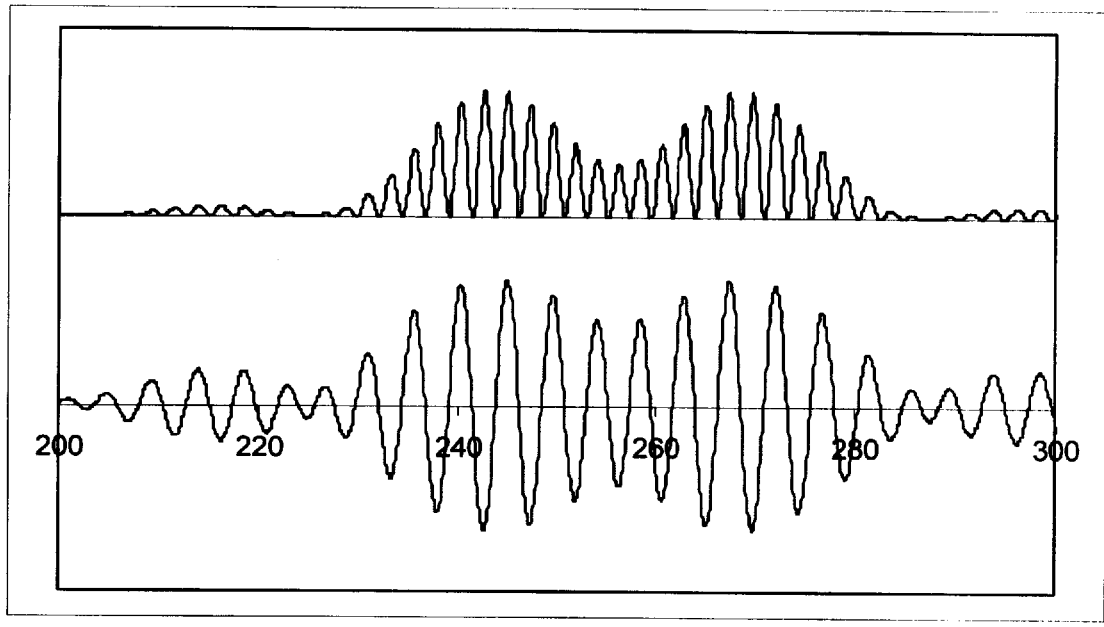
FIG. 16 (bottom) shows the convolution function of the waveform shown in FIG. 15. The top waveform is the square of the convolution waveform shown in the bottom waveform. While the two pulses appear to be displaced due to the destructive interference, the weighted convolution algorithm permits the determination of the mean transit time to within nanoseconds.

If this sinc function is considered with delay times of 250 microseconds and 262.5 microseconds, simulating dispersion as discussed previously, there will be destructive interference over part of the sinc waveform. FIG. 14 shows the shape of the arrival waveform with the vertical line showing the center of the arrival of the first sinc pulse. The destructive interference appears to move the pulse forward in time by more than an $f_0$ period. The convolution is similarly displaced, but the application of eqn. 7 to the composite convolution, which is shown in FIG. 16, results in a measured transit time within nanoseconds of the correct mean 256.25 microseconds when the summation is taken between the envelope minimums in the vicinity of 226 and 286 microseconds.

The sinc function and similar very narrow waveforms are not as robust as wider functions in that the noise interaction with fixed-frequency noise will create a signal dependent on the phase of the noise with the peak signal frequency, which is averaged out with the longer pulse widths. The resulting convolution is not symmetric about the mean arrival time and therefore the calculation of the mean from eqn. 7 is biased, although by far less than the time-of-flight calculation.

Figure 17:
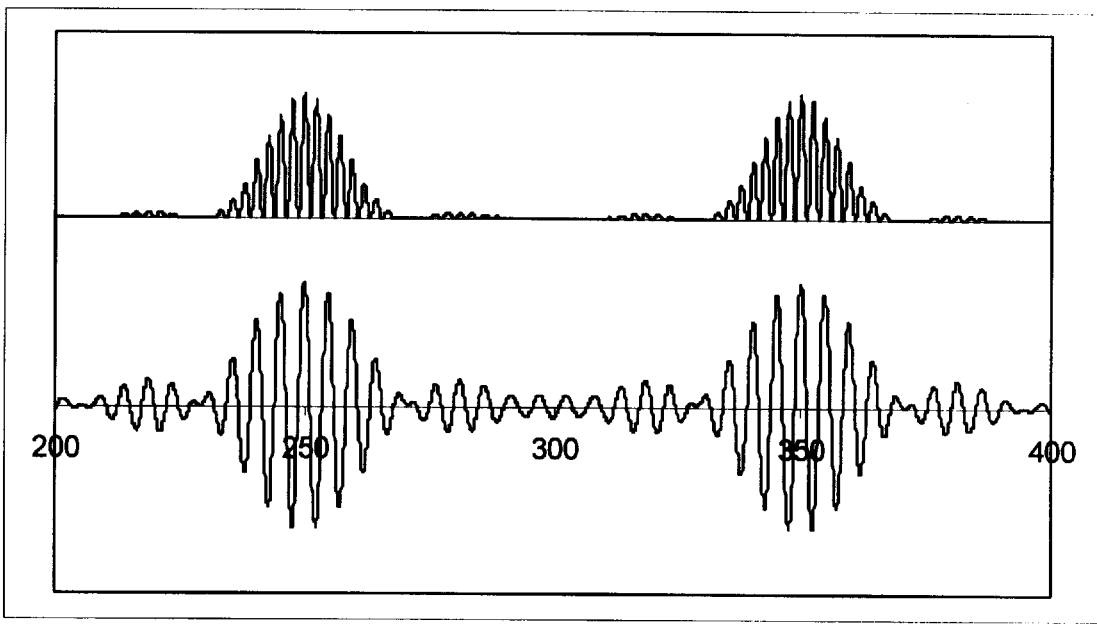
FIG. 17 represents a computer simulation of the correlation waveform (bottom) of two equal-amplitude sinc envelope waves with a linearly 37 kHz. frequency-modulated carrier frequency. The arrival times of these two pulses are 250 and 350 microseconds. The top waveform is the square of the bottom waveform and permits the resolution of the two pulses to within nanoseconds.

FIG. 17 illustrates for the sinc function described by eqn. 20 the cross correlation and squared correlation for waves with equal amplitudes arriving at 250 and 350 microseconds. For this case with non-overlapping waves the transit times for the two waves can be calculated separately by eqn. 7 or the algorithm of FIG. 19 to a high degree of accuracy.

Figure 18:
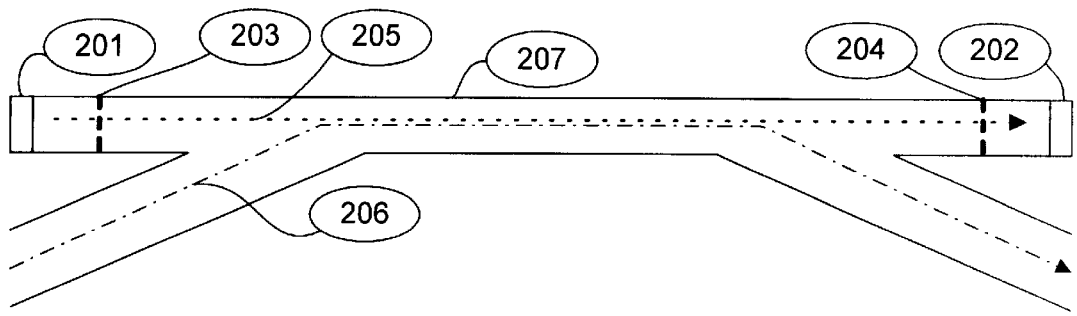
FIG. 18 illustrates one possible example of the exploitation of the ability to resolve separately arriving waves from a single source. In this figure the wave is to fill the entire flow area with the flow profile correction made by the calculations.

The accurate determination of transit times, the averaging of the transit time dispersion, and the ability to separate received pulses in time allow the use of this procedure to resolve the arrival of a transmitted pulse that is split to travel over two path lengths. One of many possible examples of this utilization of the method of calculating transit times is shown in FIG. 18, where two transducers 201 and 202 are in a pipe 207 with fluid flow 206. The wave 205 launched by 201 is shaped by a grid at 203 into a waveform filling the pipe. This grid could have holes spaced to additionally act as a Helmholtz cavity for the impedance matching of the transducer to the fluid. The grid at 204 conditions the wave for measurement by transducer 202. The use of a lower frequency $f_0$ and the wave shaping at 203 fills the fluid with the ultrasonic wave, adjusting for the flow profile, and providing a more accurate determination of the flow rate.

What is claimed is:

1. A method of calculating the transit time of ultrasonic signals for the purpose of testing a media, comprising:

transmitting a frequency-modulated ultrasonic signal into the media under test;

receiving a received ultrasonic signal ($y_n$) after transit through the media;

retrieving a reference signal $x(t)$ that is either the transmitted signal, a previously calculated received signal, or a received signal measured under reference conditions;

calculating the square of the convolution of the reference signal $x(t)$ with the received signal $(x+y)_n^2$; and determining the transit time from the square of the convolution signal, wherein the step of determining the transit time T from the convolution signal is performed with the following equation:

$$T = \frac{\int \tau \cdot [(x*y)(\tau)]^2 d\tau}{\int [(x*y)(\tau)]^2 d\tau} \approx \frac{\sum_t t \cdot \left[\sum_\tau x(\tau-t) \cdot y(\tau)\right]^2}{\sum_t \left[\sum_\tau x(\tau-t) \cdot y(\tau)\right]^2} = \frac{\sum_n t_n \cdot [(x*y)_n]^2}{\sum_n [(x*y)_n]^2}.$$

2. The method of claim 1 wherein the received signal is undersampled at a frequency much lower than the fundamental base frequency $f_0$ of the received signal before the signal is used in the step of calculating.

3. The method of claim 1 wherein the summation or integration is performed between symmetric minimums of the envelope of $(x*y)_n^2$.

4. The method of claim 1 where the summation is performed between the zero-crossings on either side of the main peak of the convolution $(x*y)_n$.

5. The method of claim 4 where the summation is over N adjacent points equally spaced in time at intervals of $$\frac{1}{2 \cdot f_o \cdot N},$$

where N>1 and $f_0$ is a fundamental base frequency.

6. The method of claim 5 where the N adjacent points are found as the maximums of $$\sum_{p=k-N+1}^{k} (x*y)_n^2.$$

7. The method of claim 5 further comprising calculating $(x*y)_n^2$ before the frequency-modulated signal is transmitted, and utilizing the results obtained from the equation $$\sum_{p=k-N+1}^{k} (x*y)_n^2$$

as a measure of the correlated noise in the system.

8. The method of claim 7 where the waveform of the frequency-modulated transmitted signal is chosen to achieve an acceptable correlated noise.

9. The method of claim 1 wherein the media is a liquid and a sufficiently low fundamental base frequency $f_0$ and an appropriate wave shape is chosen for the frequency-modulated transmitted signal such that the waveform of the frequency-modulated transmitted signal fills a liquid cross-section with the waveform so that the determination of the transit time provides an averaged transit time.

10. The method of claim 1 further comprising step of broadening areas under the main peak of the calculated convolution by performing either a deconvolution analysis on the calculated convolution or a reduction in the frequencies of the source signal when the asymmetry of the convolution in a region of interest shows the need for such deconvolution analysis or a reduction in the source frequencies in order to broaden the areas under the main peak.

11. The method of claim 1, wherein the reference signal $x(t)$ is selected to be the transmitted signal and the method further comprises performing a deconvolution of $(x*y)_n$ with an autocorrelation of reference waveform $x(t)$ to extract the transfer function $H(\omega)$ and $h(t)$; and deducing the properties of the transport medium or the paths through the media from the transfer function.

\* \* \* \* \*